(12) United States Patent
Altman et al.

(10) Patent No.: US 6,287,340 B1
(45) Date of Patent: Sep. 11, 2001

(54) BIOENGINEERED ANTERIOR CRUCIATE LIGAMENT

(75) Inventors: Gregory Altman, Medford; David Kaplan, Stow; Gordana Vunjak-Novakovic, Belmont, all of MA (US); Ivan Martin, Oberwil (CH)

(73) Assignees: Trustees of Tufts College, Boston; Massachusetts Institute of Technology, Cambridge, both of MA (US)

( * ) Notice: Subject to any disclaimer, the term of this patent is extended or adjusted under 35 U.S.C. 154(b) by 0 days.

(21) Appl. No.: 09/312,203

(22) Filed: May 14, 1999

(51) Int. Cl.[7] .................................................. A61F 2/08
(52) U.S. Cl. ................................... 623/13.11; 623/13.13; 623/13.14; 623/901
(58) Field of Search ............................. 623/13.11, 13.12, 623/13.13, 13.14, 13.17, 13.18, 901

(56) References Cited

U.S. PATENT DOCUMENTS

| | | |
|---|---|---|
| 4,467,478 | 8/1984 | Jurgutis . |
| 4,585,458 | 4/1986 | Kurland . |
| 4,597,766 | 7/1986 | Hilal et al. . |

(List continued on next page.)

FOREIGN PATENT DOCUMENTS

WO 99/33951   7/1999   (WO) .

OTHER PUBLICATIONS

Lopez Valle et al. "Peripheral anchorage of dermal equivalents", British Journal of Dermatology, 1992.*
Huang et al. "Mechanisms and Dynamics of Mechanical Strengthening in Ligament–Equivalent Fibroblast–Populated Collagen Matrices", Annals of Biomedical Eng. pp. 289–305, 1993.*
Thomas and El Haj, *Calcif. Tissue Int.* 58: 101–108 (1996).

(List continued on next page.)

*Primary Examiner*—Corrine McDermott
*Assistant Examiner*—Choon P. Koh
(74) *Attorney, Agent, or Firm*—Kevin M. Farrell (57) ABSTRACT

The present invention provides a method for producing an anterior cruciate ligament ex vivo. The method comprises seeding pluripotent stem cells in a three dimensional matrix, anchoring the seeded matrix by attachment to two anchors, and culturing the cells within the matrix under conditions appropriate for cell growth and regeneration, while subjecting the matrix to one or more mechanical forces via movement of one or both of the attached anchors. Bone marrow stromal cells are preferably used as the pluripotent cells in the method. Suitable matrix materials are materials to which cells can adhere, such as a gel made from collagen type I. Suitable anchor materials are materials to which the matrix can attach, such as Goinopra coral and also demineralized bone. Optimally, the mechanical forces to which the matrix is subjected mimic mechanical stimuli experienced by an anterior cruciate ligament in vivo. This is accomplished by delivering the appropriate combination of tension, compression, torsion, and shear, to the matrix. The bioengineered ligament which is produced by this method is characterized by a cellular orientation and/or matrix crimp pattern in the direction of the applied mechanical forces, and also by the production of collagen type I, collagen type III, and fibronectin proteins along the axis of mechanical load produced by the mechanical forces. Optimally, the ligament produced has fiber bundles which are arranged into a helical organization. The method for producing an anterior cruciate ligament can be adapted to produce a wide range of tissue types ex vivo by adapting the anchor size and attachment sites to reflect the size of the specific type of tissue to be produced, and also adapting the specific combination of forces applied, to mimic the mechanical stimuli experienced in vivo by the specific type of tissue to be produced. The methods of the present invention can be further modified to incorporate other stimuli experienced in vivo by the particular developing tissue, some examples of the stimuli being chemical stimuli, and electro-magnetic stimuli. Some examples of tissue which can be produced include other ligaments in the body (hand, wrist, elbow, knee), tendon, cartilage, bone, muscle, and blood vessels.

72 Claims, 5 Drawing Sheets

U.S. PATENT DOCUMENTS

| | | | |
|---|---|---|---|
| 4,861,733 | * | 8/1989 | White ......................................... 501/1 |
| 4,894,063 | | 1/1990 | Nashef . |
| 5,107,824 | * | 4/1992 | Rogers et al. ........................ 602/16 |
| 5,266,480 | | 11/1993 | Naughton et al. . |
| 5,445,833 | | 8/1995 | Badtkaj et al. . |
| 5,632,778 | * | 5/1997 | Goldstein .......................... 623/11.11 |
| 5,769,899 | | 6/1998 | Schwartz et al. . |
| 5,902,741 | | 5/1999 | Purchio et al. . |
| 5,928,945 | | 7/1999 | Seliktar et al. . |
| 6,121,042 | | 9/2000 | Peterson et al. . |

OTHER PUBLICATIONS

Goulet et al., Tendons and Ligaments. In *Principles of Tissue Engineering*, Ed. R. Lanza, R. Langer, W. Chick, R.G. Landes Co., pp. 633–644, R.G. Lanz Co. and Academic Press, Inc., San Diego, CA (1997).

Majumdar et al., *J. of Cellular Physio. 176*: 57–66 (1998).

Dunn, M.G., *Materials Res. Soc. Bulletin*, Nov: 43–46 (1996).

Caplan et al., Mesenchymal Stem Cells and Tissue Repair, In *The Anterior Cruciate Ligament: Current and Future Concepts*, Ed. D.W. Jackson et al., pp. 405–415, Raven Press, Ltd., New York, NY (1993).

Young et al., *J. Orthopedic Res. 16*: 406–413 (1998).

Dunn et al., *J. Biomedical Materials Res. 29*: 1363–1371 (1995).

Woods et al., *Amer. J. Sports Med. 19*: 48–55 (1991).

Freed et al., *Biotechnology and Bioengineering 43*: 605–614 (1994).

Pittenger et al., *Science 284*: 143–147 (1999).

Toyoda et al., *Clin. Ortho. and Related Res. 353*: 247–255 (1998).

Chiquet et al., *Biochem. Cell Biol. 74*: 737–744 (1996).

\* cited by examiner

LEGEND

M—MECHANICALLY STIMULATED LIGAMENT

S—STATIC CONTROL LIGAMENT

P—PERIPHERAL REGION OF LIGAMENT

C—CENTRAL REGION OF LIGAMENT

FIG. 6A

CROSS SECTIONAL AREA OF LIGAMENT INDICATING THE PERIPHERAL ZONE EXTENDING 0.638 mm FROM THE OUTER SURFACE.

FIG. 6B

HISTOLOGICAL SECTION (STIMULUS & REGION)

FIG. 6C

BIOENGINEERED ANTERIOR CRUCIATE LIGAMENT

GOVERNMENT SUPPORT

This invention was made with government support under Grant Nos. NCC8-174 and NAG9-836 awarded by the NASA. The government has certain rights in the invention.

BACKGROUND OF THE INVENTION

Every year more than 135,000 Americans tear or rupture their anterior cruciate ligament (ACL) (Chen et al., *J. Biomed. Mat. Res.* 14: 567–586 (1980); Butler, D. L., *J. Orthop. Res.* 7: 910–921 (1989); Langer et al., *Science* 260: 920–926 (1993)). The ACL serves as a primary stabilizer of anterior tibial translation and as a secondary stabilizer of valgus-varus knee angulation, and is often susceptible to rupture or tear resulting from a flexion-rotation-valgus force associated with sports injuries and traffic accidents. Ruptures or tears often result in severe limitations in mobility, pain and discomfort, and the loss of an ability to participate in sports and exercise. Failures of the ACL are classified in three categories: (1) ligamentous (ligament fibers pull apart due to tensile stress), (2) failure at the bone-ligament interface without bone fracture, and (3) failure at the bone-ligament interface with bone fracture at the attachment site of bone and ligament. The most common type of ACL failure is the first category, ligamentous.

Total surgical replacement and reconstruction are required when injury to the ACL involves significant tear or rupture. Four options have been utilized for repair or replacement of a damaged ACL: (1) autografts, (2) allografts, (3) xenografts, and (4) synthetic prostheses (degradable and non-degradable). To date, no surgical repair procedure has been shown to restore knee function completely, and novel treatment options would likely benefit a large number of patients.

The problems associated with the use of synthetic ACL replacements, along with the limited availability of the donor tissue, have motivated research towards the development of functional and biocompatible equivalents of native tissues. This shift from synthetic to biologically-based ACL replacements first applied in early studies in which collagenous ACL prostheses were prepared as composite structures consisting of reconstituted type I collagen fibers in a collagen I matrix with polymethylmethacrylate bone fixation plugs, and used as anterior cruciate ligament replacement tissues in rabbits (Dunn et al., *Am. J. Sports Medicine* 20: 507–515 (1992)). Subsequent studies incorporated active biological components into the process, such as ligament fibroblasts seeded on cross-linked collagen fiber scaffolds that were used as ligament analogs (Dunn et al., *J. Biomedical Materials Res.* 29: 1363–1371 (1995); Dunn, M. G., *Materials Res. Soc. Bulletin, Nov:* 43–46 (1996)), and suggested that structures approximating native ligaments can be generated. A tendon gap model, based on pre-stressed collagen sutures seeded with mesenchymal stem cells provided improved repair of large tendon defects (Young et al., 1998). Goulet et al. modified the collagen-fibroblast system by using ligament fibroblasts in non-cross-linked collagen, with bone anchors to pre-stress the tissue and facilitate surgical implantation (Goulet et al., Tendons and Ligaments. In *Principles of Tissue Engineering*, Ed. R. Lanza, R. Langer, W. Chick. R. G. Landes Co. pp 633–643, R. G. Lanz Co. and Academic Press, Inc., San Diego, Calif. (1997)). Passive tension produced by growing the new ligament in a vertical position induced fibroblast elongation and the alignment of the cells and surrounding extracellular matrix.

However, to date, no human clinical trials have been reported with tissue culture bioengineered anterior cruciate ligaments. This is due to the fact that each approach has failed to address one or more of the following issues: (1) the lack of a readily available cell or tissue source, (2) the unique structure (e.g. crimp pattern, peripheral helical pattern and isometric fiber organization) of an ACL, and (3) the necessary remodeling time in vivo for progenitor cells to differentiate and/or autologous cells to infiltrate the graft, thus extending the time a patient must incur a destabilized knee and rehabilitation. The development of methods for generating more fully functional bioengineered anterior cruciate ligaments would greatly benefit the specific field of knee reconstructive surgery, and would also provide wider benefits to the overall field of in vitro tissue generation and replacement surgery.

SUMMARY OF THE INVENTION

The present invention provides a method for producing an anterior cruciate ligament ex vivo. The method comprises seeding pluripotent stem cells in a three dimensional matrix, anchoring the seeded matrix by attachment to two anchors, and culturing the cells within the matrix under conditions appropriate for cell growth and regeneration, while subjecting the matrix to one or more mechanical forces via movement of one or both of the attached anchors. In a preferred embodiment, the pluripotent cells are bone marrow stromal cells. Suitable matrix materials are materials to which cells can adhere. A preferred matrix material is collagen type I gel. Suitable anchor materials are materials to which the matrix can attach. Preferred anchor material includes Goinopra coral which has been treated to convert the calcium carbonate to calcium phosphate, and also demineralized bone. In a preferred embodiment, the mechanical forces to which the matrix is subjected mimic mechanical stimuli experienced by an anterior cruciate ligament in vivo. This is accomplished by delivering the appropriate combination of tension, compression, torsion, and shear, to the matrix.

Another aspect of the present invention is the bioengineered ligament which is produced by the above method. The ligament is characterized by a cellular orientation and/or matrix crimp pattern in the direction of the applied mechanical forces, and also by the production of collagen type I, collagen type III, and fibronectin proteins along the axis of mechanical load produced by the mechanical forces. In a preferred embodiment, the ligament is characterized by the presence of fiber bundles which are arranged into a helical organization.

Another aspect of the present invention is a method for producing a wide range of ligament types ex vivo using an adaptation of the method for producing an anterior cruciate ligament by adapting the anchor size to reflect the size of the specific type of ligament to be produced, and also adapting the specific combination of forces applied, to mimic the mechanical stimuli experienced in vivo by the specific type of ligament to be produced. Similar adaptations of the method can be made to produce other tissues ex vivo from pluripotent stem cells, by adapting the mechanical forces applied during cell culture to mimic stresses experienced in vivo by the specific tissue type to be produced. The methods of the present invention can be further modified to incorporate other stimuli experienced in vivo by the particular developing tissue, some examples of the stimuli being chemical stimuli, and electromagnetic stimuli.

Another aspect of the present invention relates to the specific tissues which are produced by the methods of the present invention. Some examples of tissue which can be produced include other ligaments in the body (hand, wrist, elbow, knee), cartilage, bone, tendon, muscle, and blood vessels.

DETAILED DESCRIPTION OF THE INVENTION

The present invention is based on the finding that the histomorphological properties of an in vitro produced bioengineered tissue generated from pluripotent cells within a matrix are affected by the direct application of mechanical force to the matrix during tissue generation. This discovery provides important new insights into the relationship between mechanical stress, biochemical and cell immobilization methods, and cell differentiation, and has applications in producing a wide variety of tissues in vitro from pluripotent cells.

One aspect of the present invention relates to a method for producing an anterior cruciate ligament (ACL) ex vivo. Cells capable of differentiating into ligament cells are grown under conditions which simulate the movements and forces experienced by an ACL in vivo through the course of embryonic development into mature ligament function. This is accomplished by the following steps: Under sterile conditions, pluripotent cells are seeded within a three dimensional matrix, of cylindrical shape, which is comprised of a material to which the cells can adhere (e.g. collagen gel). The faces of the matrix cylinder are each attached to respective anchors, through which a range of forces are to be applied to the matrix. To facilitate force delivery to the matrix, it is preferable that the entire surface of each respective face of the matrix contact the face of the respective anchors. Anchors with a shape which reflects the site of attachment (e.g. cylindrical) are best suited for use in this method. Once assembled, the cells in the anchored matrix are cultured under conditions appropriate for cell growth and regeneration. The matrix is subjected to one or more mechanical forces applied through the attached anchors (e.g. via movement of one or both of the attached anchors) during the course of culture.

In the experiments described in the Exemplification section below, the applied mechanical stimulation was shown to dramatically influence the morphology, and cellular organization of the progenitor cells within the resulting tissue. The extracellular matrix components secreted by the cells and organization of the extra cellular matrix throughout the tissue was also significantly influenced by the forces applied to the matrix during tissue generation. During in vitro tissue generation the cells and extra cellular matrix aligned along the axis of load, reflecting the in vivo organization of a native ACL which is also along the various load axes produced from natural knee joint movement and function. These results suggest that the physical stimuli experienced in nature by cells of developing tissue, such as the ACL, play a significant role in progenitor cell differentiation and tissue formation. They further indicate that this role can be effectively duplicated in vitro by mechanical manipulation to produce a similar tissue. The more closely the forces produced by mechanical manipulation resemble the forces experienced by an ACL in vivo, the more closely the resultant tissue will resemble a native ACL.

One or more types of pluripotent cells are used in the method. Such cells have the ability to differentiate into a wide variety of cell types in response to the proper differentiation signals. More specifically, the method requires cells which have the ability to differentiate into cells of ligament tissue. In a preferred embodiment, bone marrow stromal cells, also known as mesenchymal cells are used. If the resulting bioengineered ligament is to be transplanted into a patient, the cells should be derived from a source which is compatible with the intended recipient. The recipient will generally be a human, although applications in veterinary medicine also exist. In one embodiment, the cells are obtained from the recipient, although compatible donor cells may also be used. The determination of compatibility is within the means of the skilled practitioner.

The three dimensional matrix used in the method is potentially comprised of any material to which the cells can adhere. This matrix serves as a preliminary matrix, which is supplemented and possibly even replaced by extracellular matrix components produced by the differentiating cells. Use of a more specialized matrix may enhance or accelerate the development of the ACL. For instance, a matrix which has specific mechanical properties (e.g. increased tensile strength) can withstand strong forces prior to reinforcement from cellular extracellular matrix components. Other properties which may also be useful in a preliminary matrix include, without limitation, biocompatibility and susceptibility to biodegradation.

The matrix used in the examples disclosed herein was a collagen gel. One of skill in the art will recognize that the properties of the preliminary matrix can be modulated and enhanced by modifying the matrix components, and that use of an enhanced matrix is likely to increase the efficiency of production of a bioengineered ACL. Such modifications include, without limitation, modifications aimed at modulating the mechanical and mass transport properties of the matrix. In particular, the concentration of collagen and the degree of crosslinking of collagen in the matrix can significantly influence the mechanical properties of the matrix, as well as the diffusional transport rates of nutrients and large molecules. Since the ACL is made primarily of collagen type I, it is particularly well suited for use as a preliminary matrix component. The concentration of collagen type I in the matrix should be sufficient to support cell adhesion, proliferation and differentiation. In one embodiment, collagen type I is used at a final concentration from about 2 mg/ml to about 6 mg/ml. In another embodiment the final concentration of collagen type I in the matrix is about 2 mg/ml. In another embodiment, the collagen in the preliminary matrix is crosslinked. Suitable processes for cross linking collagen include without limitation, dehydrothermal crosslinking and ultraviolet irradiation crosslinking. Other suitable matrix materials include, without limitation polysaccharides, alginates, other proteins such as silk and elastin, synthetic polymers such as polyglycolic acid and polylactic acid and copolymers of the two, and demineralized bone.

The cells are seeded within the preliminary matrix either pre- or post-matrix formation, depending upon the particular matrix used and the method of matrix formation. Uniform seeding is preferable. In theory, the number of cells seeded does not limit the final ligament produced, however optimal seeding may increase the rate of generation. optimal seeding amounts will depend on the specific culture conditions. In one embodiment, the matrix is seeded with from about 0.05 to 5 times the physiological cell density of a native ligament.

The seeded matrix is subjected to mechanical forces which are applied through a set of attached anchors. Anchors are defined herein as comprising a solid surface to which force can be applied and transmitted to an attached matrix. The anchors must be made of a material suitable for matrix attachment, and the resulting attachment should be strong enough to endure the stress of the mechanical forces applied. The preliminary matrix must be able to attach to the anchors. In addition, it is preferable that the anchors be of a material which is suitable for the attachment of extracellular matrix which is produced by the differentiating cells. Some examples of suitable anchor material include, without limitation, Goinopra coral and demineralized bone. In a preferred embodiment, the anchors are Goinopra coral which has a pore size of 500 $\mu$M, and the coral is treated by means to convert the calcium carbonate of the coral to calcium phosphate, prior to use.

Alternatively, anchor material may be created or further enhanced by infusing a selected material with a factor which promotes matrix binding. The term infuse is considered to include any method of application which appropriately distributes the factor onto the anchor (e.g. coating, permeating, contacting). Examples of such factors include without limitation, laminin, fibronectin, any extracellular matrix protein that promotes adhesion, silk, factors which contain arginine-glycine-aspartate peptide binding regions. Growth factors or bone morphogenic protein can also be used to enhance anchor attachment. In addition, anchors may be pre-seeded with cells (e.g. stem cells, ligament cells, osteoblasts) which adhere to the anchors and bind the matrix, to produce enhanced matrix attachment.

The matrix is attached to the anchors via contact to the anchor face or alternatively by actual penetration of the matrix material through the anchor material. Because the force applied dictates the final ligament produced and the force is applied through the anchors, the size of the final ligament produced is in part dictated by the size of the attachment site of the anchor. One of skill in the art will appreciate that an anchor of appropriate size to the desired final ligament should be used. A preferred anchor shape for the formation of an ACL is a cylinder, however, one of skill in the art will appreciate that other anchor shapes and sizes will also function adequately. In a preferred embodiment, anchors have an appropriate size and composition for direct insertion into bone tunnels in the femur and tibia of a recipient.

The cells are cultured within the matrix under conditions appropriate for cell growth and differentiation. During the culture process, the matrix is subjected to one or more mechanical forces via movement of one or both of the attached anchors. The mechanical forces of tension, compression, torsion and shear, and combinations thereof, are applied in the appropriate combinations, magnitudes, and frequencies to mimic the mechanical stimuli experienced by an ACL in vivo.

Various factors will influence the amount of force which can be tolerated by the matrix (e.g. matrix composition, cell density). Matrix strength is expected to change through the course of tissue development. Therefore, mechanical forces applied will increase or decrease in magnitude, duration, and variety over the period of ligament generation, to appropriately correspond to matrix strength at the time of application.

The more accurate the intensity and combination of stimuli applied to the matrix during tissue development, the more the resulting ligament will resemble a native ACL. Two issues must be considered regarding the natural function of the ACL when devising the in vitro mechanical force regimen that closely mimics the in vivo environment, (1) the different types of motion experienced by the ACL and the responses of the ACL to knee joint movements and (2) the extent of the mechanical stresses experienced by the ligament. Specific combinations of mechanical stimuli are generated from the natural motions of the knee structure and transmitted to the native ACL. To briefly describe the motions of the knee, the connection of the tibia and femur by the ACL between provides six degrees of freedom when considering the motions of the two bones relative to each other: the tibia can move in the three directions and can rotate relative to the axes for each of these three directions. The knee is restricted from achieving the full ranges of these six degrees of freedom due to the presence of ligaments and capular fibers and the knee surfaces themselves (Biden et al., Experimental methods used to evaluate knee ligament function. In *Knee Ligaments: Structure, Function, Injury and Repair*, Ed. D. Daniel et al. Raven Press, pp.135–151 (1990)). Small translational movements are also possible. The attachment sites of the ACL are responsible for its stabilizing roles in the knee joint. The ACL functions as a primary stabilizer of anterior-tibial translation, and as a secondary stabilizer of valgus-varus angulation, and tibial rotation (Shoemaker et al., The limits of knee motion. In *Knee Ligaments: Structure, Function, Injury and Repair*, Ed. D. Daniel et al. Raven Press, pp.1534–161 (1990)). Therefore, the ACL is responsible for stabilizing the knee in three of the six possible degrees of freedom. As a result, the ACL has developed a specific fiber organization and overall structure to perform these stabilizing functions. The present invention simulates these conditions in vitro to produce a tissue with similar structure and fiber organization.

The extent of mechanical stresses experienced by the ACL can be similarly summarized. The ACL undergoes cyclic loads of about 300 N between one and two million cycles per year. It is also critical to consider linear stiffness (~182 N/mm), ultimate deformation (100% of ACL) and energy absorbed at failure (12.8 N-m) (Woo et al., The tensile properties of human anterior cruciate ligament (ACL) and ACL graft tissues. In *Knee Ligaments: Structure, Function, Injury and Repair*, Ed. D. Daniel et al. Raven Press, pp.279–289 (1990)) when developing an ACL surgical replacement.

The Exemplification section below details the production of a prototype bioengineered anterior cruciate ligament (ACL) ex vivo. Mechanical forces mimicking a subset of the mechanical stimuli experienced by a native ACL in vivo (rotational deformation and linear deformation) were applied in combination, and the resulting ligament which was formed was studied to determine the effects of the applied forces on tissue development. Exposure of the developing ligament to physiological loading during in vitro formation induced the cells to adopt a defined orientation along the axes of load, and to generate extracellular matrices along the axes as well. These results indicate that the incorporation of additional mechanical forces into the regime to produce a more complex network of load axes that more accurately mimics the environment of the native ACL, will produce a bioengineered ligament which more closely resembles a native ACL. The different mechanical forces to be applied include, without limitation, tension, compression, torsion, and shear. These forces are applied in combinations which simulate forces experienced by an ACL in the course of natural knee joint movements and function. These movements include, without limitation, knee joint extension and flexion as defined in the coronal and sagittal planes, and knee joint flexion. Optimally, the combination of forces applied mimics the mechanical stimuli experienced by an anterior cruciate ligament in vivo as accurately as is experimentally possible. Varying the specific regimen of force application through the course of ligament generation is expected to influence the rate and outcome of tissue development, with optimal conditions to be determined empirically. Potential variables in the regimen include, without limitation: (1) strain rate, (2) repetition number, (3) duration at extreme points of ligament deformation, (4) force levels, and (5) different force combinations. It will be recognized by one of skill in the art that a potentially unlimited number of variations exist. In a preferred embodiment the regimen of mechanical forces applied produces helically organized fibers similar to those of the native ligament, described below.

The fiber bundles of a native ligament are arranged into a helical organization. The mode of attachment and the need for the knee joint to rotate ~140° of flexion has resulted in the native ACL inheriting a 90° twist and with the peripheral fiber bundles developing a helical organization. This unique biomechanical feature allows the ACL to sustain extremely high loading. In the functional ACL, this helical organization of fibers allows anterior-posterior and posterior-anterior fibers to remain relatively isometric in respect to one another for all degrees of flexion, thus stabilizing the knee throughout all ranges of joint motion. In a preferred embodiment of the invention, mechanical forces which simulate a combination of knee joint flexion and knee joint extension are applied to the developing ligament to produce an engineered ACL which possesses this same helical organization. The mechanical apparatus used in the experiments presented in the Exemplification below provides control over strain and strain rates (both translational and rotational). An improved mechanical apparatus will monitor the actual load experienced by the growing ligaments, serving to 'teach' the ligaments over time through monitoring and increasing the loading regimes. Such a reactor can be designed by starting from the features of the first generation bioreactor used in the Experiments described in the Exemplification section below. To these features (e.g., ports for medium and gas exchange, sterilizable) will be added features, including e.g. a flexibility to run multiple mechanical deformation programs concurrently. Such a system should have a precise (strain-gauge) control of the applied forces, and an on-line monitoring and control of mechanical loading parameters.

Another aspect of the present invention relates to the bioengineered anterior cruciate ligament produced by the above described methods. The bioengineered ligament produced by these methods is characterized by cellular orientation and/or a matrix crimp pattern in the direction of the mechanical forces applied during generation. The ligament is also characterized by the production/presence of extra cellular matrix components (e.g. collagen type I, and type III, elastin, and fibronectin proteins) along the axis of mechanical load experienced during culture. In a preferred embodiment, the ligament fiber bundles are arranged into a helical organization, as discussed above.

The above methods are not limited to the production of an ACL, but can also be used to produce other ligaments found in the knee (e.g. posterior cruciate ligament) or other parts of the body (e.g. hand, wrist, ankle, elbow and shoulder). All moveable joints in a human body have specialized ligaments which connect the articular extremities of the bones in the joint. Each ligament in the body has a specific structure and organization which is dictated by its function and environment. The various ligaments of the body, their locations and functions are listed in *Anatomy, Descriptive and Surgical* (Gray, H. , Eds. Pick, T. P., Howden, R., Bounty Books, New York (1977)) the pertinent contents of which are incorporated herein by reference. By determining the physical stimuli experienced by a given ligament, and incorporating forces which mimic these stimuli, the above described method for producing an ACL ex vivo can be adapted to produce a bioengineered ligament ex vivo which simulates any ligament in the body.

The specific type of ligament to be produced is predetermined prior to ligament generation since several aspects of the method vary with the specific conditions experienced in vivo by the native ligament. The mechanical forces to which the developing ligament is subjected during cell culture are determined for the particular ligament type being cultivated. The specific conditions can be determined by those skilled in the art by studying the native ligament and its environment and function. One or more mechanical forces experienced by the ligament in vivo are applied to the matrix during culture of the cells in the matrix. The skilled practitioner will recognize that a ligament which is superior to those currently available can be produced by the application of a subset of forces experienced by the native ligament. However, optimally, the full range of in vivo forces will be applied to the matrix in the appropriate magnitudes and combinations to produce a final product which most closely resembles the native ligament. These forces include, without limitation, the forces described above for the production of an ACL. Because the mechanical forces applied vary with ligament type, and the final size of the ligament will be influenced by the anchors used, optimal anchor composition, size and matrix attachment sites are to be determined for each type of ligament by the skilled practitioner.

Another aspect of the present invention relates to the production of other tissue types ex vivo using methods similar to those described above for the generation of ligaments ex vivo. The above described methods can also be applied to produce a range of engineered tissue products which involve mechanical deformation as a major part of their function, such as tendon, muscle (e.g. smooth muscle, skeletal muscle, cardiac muscle), bone, cartilage, vertebral discs, and some types of blood vessels. Bone marrow stomal cells possess the ability to differentiate into these as well as other tissues. The results present in the Exemplification section below indicate that growth in an environment which mimics the specific mechanical environment of a given tissue type will induce the appropriate cell differentiation to produce a bioengineered tissue which significantly resembles native tissue. The ranges and types of mechanical deformation of the matrix can be extended to produce a wide range of tissue structural organization. Preferably, the cell culture environment reflects the in vivo environment experienced by the native tissue and the cells it contains, throughout the course of embryonic development to mature function of the cells within the native tissue, as accurately as possible. Factors to consider when designing specific culture conditions to produce a given tissue include, without limitation, the matrix composition, the method of cell immobilization, the anchoring method, the specific forces applied, and the cell culture medium. The specific regimen of mechanical stimulation depends upon the tissue type to be produced, and is established by varying the application of mechanical forces (e.g. tension only, torsion only, combination of tension and torsion, with and without shear, etc.), the force amplitude (e.g. angle or elongation), the frequency and duration of the application, and the duration of the periods of stimulation and rest.

The method for producing the specific tissue type ex vivo is an adaptation of the above described method for producing an ACL. Components involved include pluripotent cells, a three dimensional matrix to which cells can adhere, and a plurality of anchors which have a face suitable for matrix attachment. The pluripotent cells (preferably bone marrow stroma cells) are seeded in the three dimensional matrix by means to uniformly immobilize the cells within the matrix. As discussed above, the only requirement for the matrix is that it be of a substance, or contain a substance, to which the cells can adhere, although certain matrix compositions will most likely prove optimal for specific tissues. Matrix shape is not viewed as a limiting factor to the method, however, a specific shape which resembles the final desired product may facilitate generation of the tissue. The number of cells seeded is also not viewed as limiting, however, seeding the matrix with a high density of cells may accelerate tissue generation.

Once seeded, the matrix is attached to a plurality of anchors. The number of anchors, as well as their shape, and the shape and size of their sites of attachment to the matrix, depends upon the particular tissue being produced, and will reflect the nature of the forces applied to the matrix. For some tissues (e.g. cartilage, bone, vertebral discs), use of a solid matrix (e.g. demineralized bone or Goinopra coral) will be optimal. Because mechanical forces can be applied directly to a solid matrix, solid matrices may be considered herein to possess inherent anchors. If deemed necessary, the location and size of these inherent anchors is determined by the position and area of the solid matrix to which the mechanical force is applied.

The specific forces applied are to be determined for each tissue type produced through examination of native tissue and the mechanical stimuli experienced in vivo. A given tissue type experiences characteristic forces which are dictated by location and function of the tissue within the body. For instance, cartilage is known to experience a combination of shear and compression/tension in vivo, bone experiences compression. Determination of the specific mechanical stimuli experienced in vivo by a given tissue is within the means of one of skill in the art.

Additional stimuli (e.g. chemical stimuli, electromagnetic stimuli) can also be incorporated into the above described methods for producing bioengineered ligaments and other tissues. Cell differentiation is known to be influenced by chemical stimuli from the environment, often produced by surrounding cells, such as secreted factors, cell-cell contact, chemical gradients, and specific pH levels, to name a few. Other more unique stimuli are experienced by more specialized types of tissues (e.g. the electrical stimulation of cardiac muscle). The application of such tissue specific stimuli in concert with the appropriate mechanical forces is expected to facilitate differentiation of the cells into a tissue which more closely approximates the specific natural tissue.

Tissues produced by the above described methods provide an unlimited pool of tissue equivalents for surgical implantation into a compatible recipient. Engineered tissues may also be utilized for in vitro studies of normal or pathological tissue function, e.g. for in vitro testing of cell- and tissue-level responses to molecular, mechanical, or genetic manipulations. For example, tissues based on normal or transfected cells can be used to assess tissue responses to biochemical or mechanical stimuli, identify the functions of specific genes or gene products that can be either over-expressed or knocked-out, or to study the effects of pharmacological agents. Such studies will likely provide more insight into ligament development, normal and pathological function, and eventually lead toward fully functional tissue engineered replacements, based in part on already established tissue engineering approaches, new insights into cell differentiation and tissue development, and the use of mechanical regulatory signals in conjunction with cell-derived and exogenous biochemical factors to improve structural and functional tissue properties.

The production of engineered tissues such as ligaments has the potential for applications such as harvesting bone marrow stoma cells from individuals at high risk for tissue injury (e.g. ACL rupture) prior to injury. These cells could be either stored until needed or seeded into the appropriate matrix and cultured and differentiated in vitro under mechanical stimuli to produce a variety of bioengineered prosthetic tissues to be held in reserve until needed by the donor. The use of bioengineered living tissue prosthetics that better match the biological environment in vivo, provide the required physiological loading to sustain for example, the dynamic equilibrium of a normal, fully functional ligament, should reduce rehabilitation time for a recipient of a prosthesis from months to weeks, particularly if the tissue is pre-grown and stored. Benefits include a more rapid regain of functional activity, shorter hospital stays, and fewer problems with tissue rejections and failures.

Exemplification

The feasibility of using directly applied forces during tissue cultivation to promote in vitro formation of ACL-like structures was tested. A three-dimensional tissue culture system was developed utilizing precursor cells, obtained from bone marrow stroma, immobilized in a collagen gel matrix. The matrix was positioned within a bioreactor that subjected the matrix to defined types, magnitudes and frequencies of mechanical forces, corresponding in part to those experienced by an ACL during physiological loading in vivo. Cells within the matrix were cultured under conditions appropriate for proliferation during exposure of the matrix to the various mechanical forces, to produce a bioengineered anterior cruciate ligament ex vivo. Control tissues were cultured with no mechanical stimulation of the matrix under otherwise identical conditions.

A bioreactor that would provide a reasonable range of mechanical options for deformation of the growing ligaments was constructed. The reactor provided tensile/compressive and torsional loads along the longitudinal axis and could accommodate up to 12 individual reactor tubes for the growth of ligaments. Although this reactor did not subject the growing ligament to the full range of deformations experienced in vivo, the information obtained from these preliminary experiments can be used to design a more advanced reactor.

Figure 1:
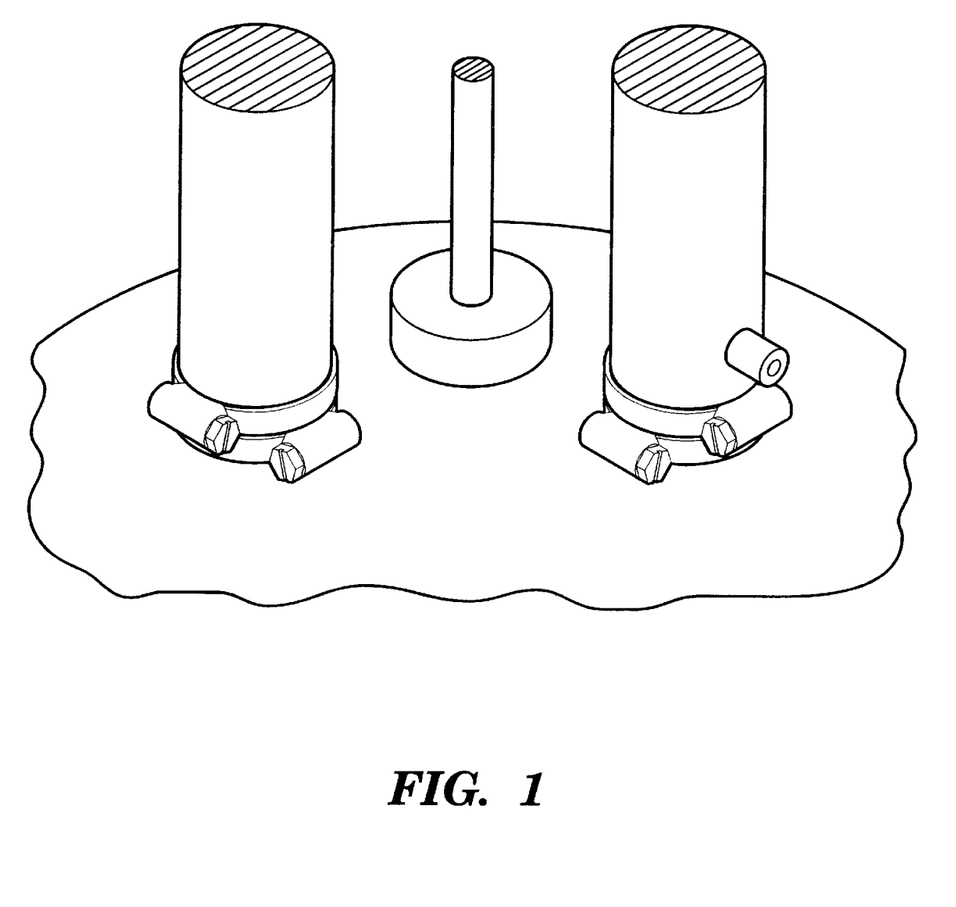
FIG. 1 is a picture of bioreactor tubes containing growing ligaments.
Figure 2:
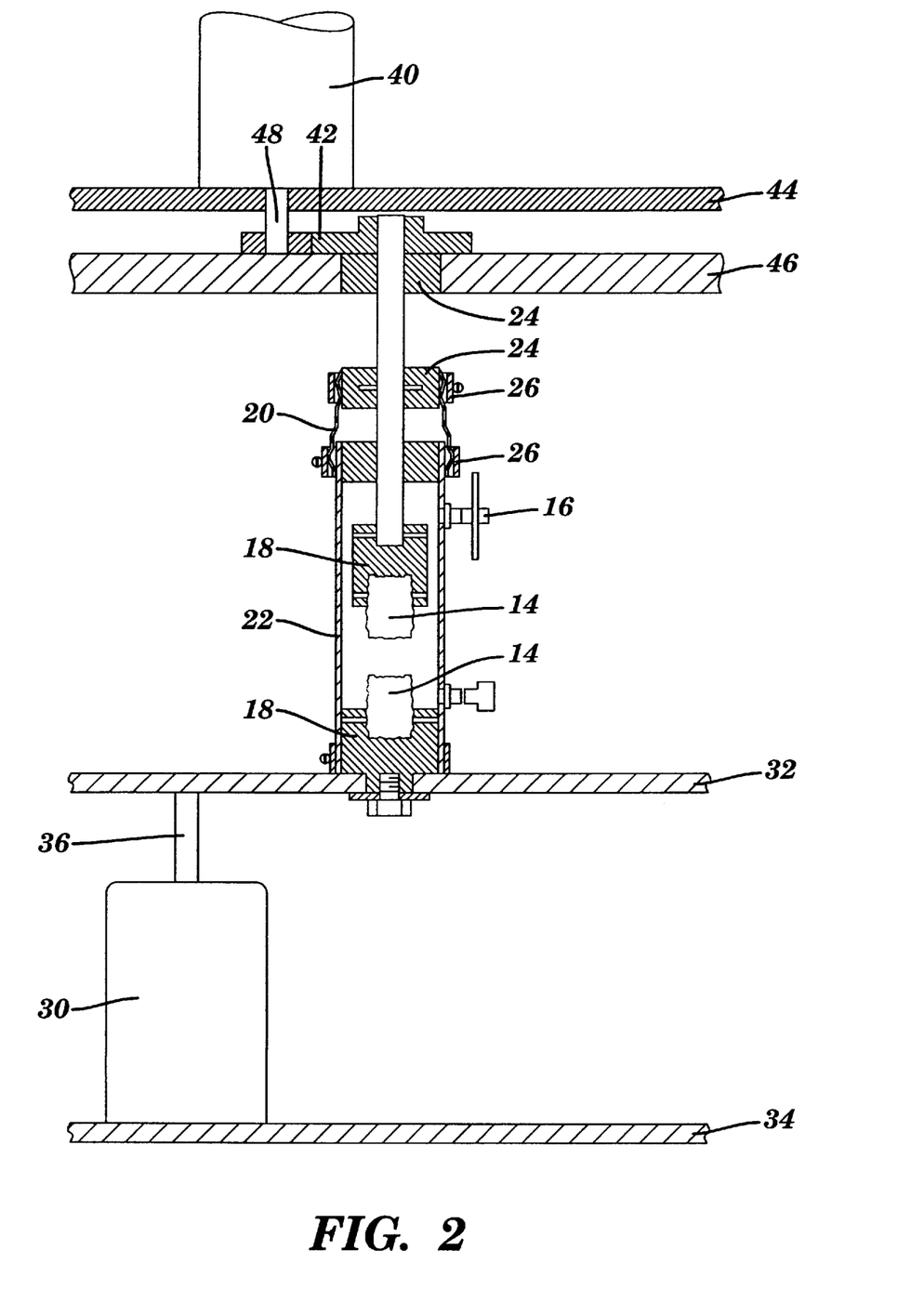
FIG. 2 is a schematic of the mechanical apparatus with an attached bioreactor tube.
Figure 3:
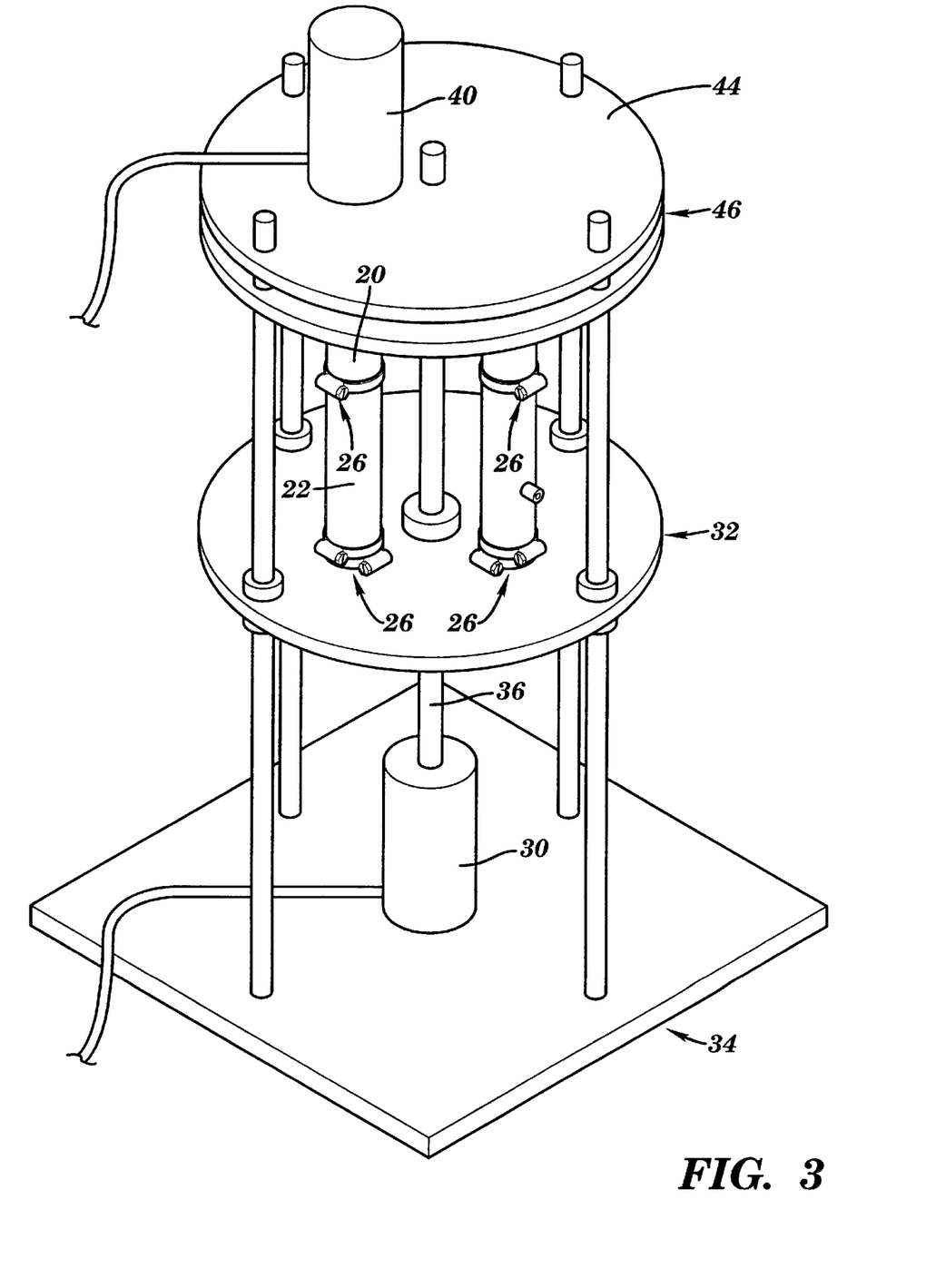
FIG. 3 is a picture of an actual mechanical apparatus with attached reactor tubes containing growing ligaments.

The two major parts of the device included: (1) the bioreactor tubes which provide the growth environment and attachment sites for the growing ligaments (shown in FIG. 1), and (2) the mechanical apparatus to provide mechanical loading regimes to the bioreactor tubes. FIG. 2 presents a schematic of the mechanical apparatus and FIG. 3 is a picture of the working device.

Experiment 1

The first experiment was performed to better characterize adhesion of the collagen matrix to the coral anchors. This experiment ran for a total of 12 days and encompassed rotational deformation of 10° initially, increasing to 65° by the end of the experiment. The linear deformation was 0.5 mm along the longitudinal axis of the ligament for the majority of the 12 days. No loss of adhesion between the collagen matrix and the coral anchors was observed, indicating that at least a 65° rotational deformation could be tolerated by present system.

Experiment 2

Figure 4:
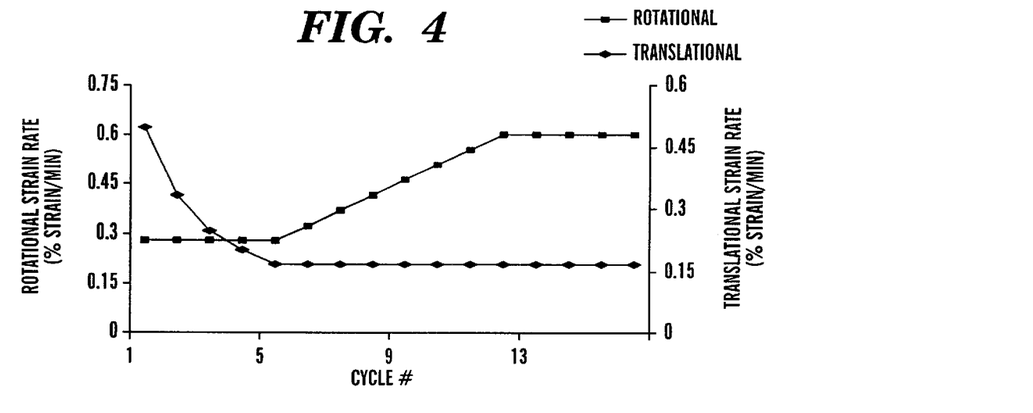
FIG. 4 is a diagrammatic representation of the rotational strain rates and the translational strain rates experienced by the growing ligaments in Experiment 2.

The next set of experiments were conducted to study the effects of increased mechanical stresses on the growing ligaments. Linear deformation was kept constant at 1 mm (double that of Experiment 1) throughout the 13 day experiment while rotational deformation was increased progressively from 10° to 65° by the end of the experiment. The time to progress from one rotational extreme to the other extreme was maximally 30 minutes, with rests at the extreme points varying from 0 to 3 hours over the course of the experiment. Thus, complete cycles of mechanical deformation ranged from 0.33 hr to 4 hr. A detailed description of the mechanical processes employed in this experiment is shown below to illustrate the range of control over the bioreactor that we can achieve with the apparatus (Table 1). FIG. 4 summarizes the rotational and translational strain rates used in this experiment.

Histology was performed on the resulting tissue to examine cell morphology. Ligament tissue samples were stained with hemotoxylin and eosin and visualized by light microscopy at 400×. Results indicated that approximately 50% of the cells from the mechanically stimulated ligaments exhibited ovid morphology and alignment along the longitudinal axis of the ligament. Immunohistochemistry was not performed.

TABLE 1

Mechanical stresses applied to the ligaments in the bioreactors during Experiment 2. Note: cycle 1 provided an initial 24 hr rest period.

| Cycle # | $\Delta L_r$ Degrees | $\Delta L_t$ mm | Duration To/From Extreme Position min | Extreme Position Rest hrs | Home Position Rest hrs | Duration For One Complete Repetition hrs | Repetition # | Total Cycle Time Days | Time from Start of Experiment Days |
|---|---|---|---|---|---|---|---|---|---|
| 1 | 0 | 0 | 0 | 0 | 0 | 24 | 1 | 1 | 1 |
| 2 | 10 | 1 | 10 | 0 | 0 | 0.33 | 36 | 0.5 | 1.5 |
| 3 | 15 | 1 | 15 | 0 | 0 | 0.50 | 24 | 0.5 | 2.0 |
| 4 | 20 | 1 | 20 | 0 | 0 | 0.67 | 18 | 0.5 | 2.5 |
| 5 | 25 | 1 | 25 | 0 | 0 | 0.83 | 14 | 0.5 | 3.0 |
| 6 | 30 | 1 | 30 | 0 | 0 | 1 | 12 | 0.5 | 3.5 |
| 7 | 35 | 1 | 30 | 0 | 0 | 1 | 12 | 0.5 | 4.0 |
| 8 | 40 | 1 | 30 | 0 | 0 | 1 | 12 | 0.5 | 4.5 |
| 9 | 45 | 1 | 30 | 0 | 0 | 1 | 12 | 0.5 | 5.0 |
| 10 | 50 | 1 | 30 | 0 | 0 | 1 | 12 | 0.5 | 5.5 |
| 11 | 55 | 1 | 30 | 0 | 0 | 1 | 12 | 0.5 | 6.0 |
| 12 | 60 | 1 | 30 | 1 | 0 | 2 | 24 | 2 | 8.0 |
| 13 | 65 | 1 | 30 | 1 | 0 | 2 | 12 | 1 | 9.0 |
| 14 | 65 | 1 | 30 | 1.5 | 0 | 2.5 | 10 | 1 | 10.0 |
| 15 | 65 | 1 | 30 | 2 | 0 | 3 | 8 | 1 | 11.0 |
| 16 | 65 | 1 | 30 | 2.5 | 0 | 3.5 | 7 | 1 | 12.0 |
| 17 | 65 | 1 | 30 | 3 | 0 | 4 | 6 | 1 | 13.0 |

Experiment 3

Figure 5A:
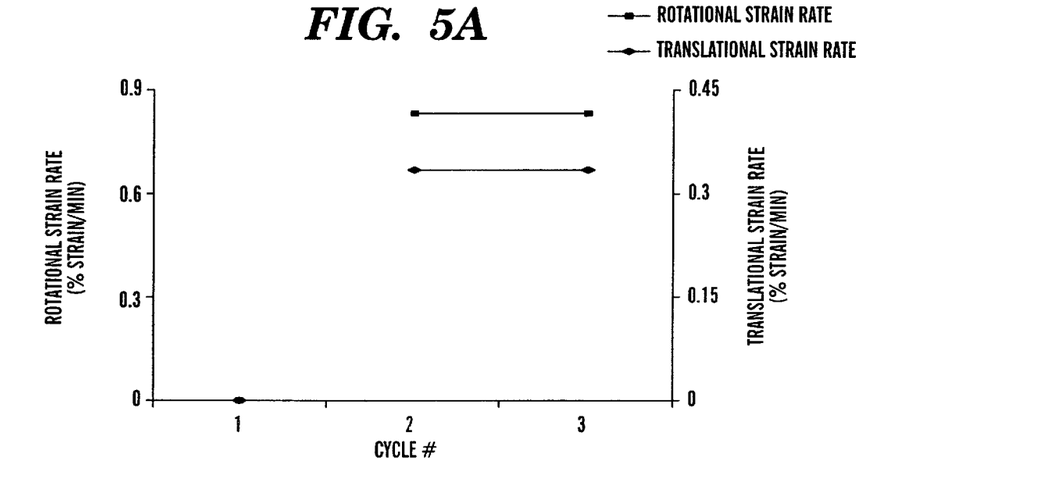
FIGS. 5 contains diagrammatic representations of the mechanical regime applied to the growing ligaments in Experiment 3. *a*) Indicates the rotational and translational strain rates as a % of strain over time (min). *b*) Indicates rotational and linear deformation experienced over the course of time.
Figure 5B:
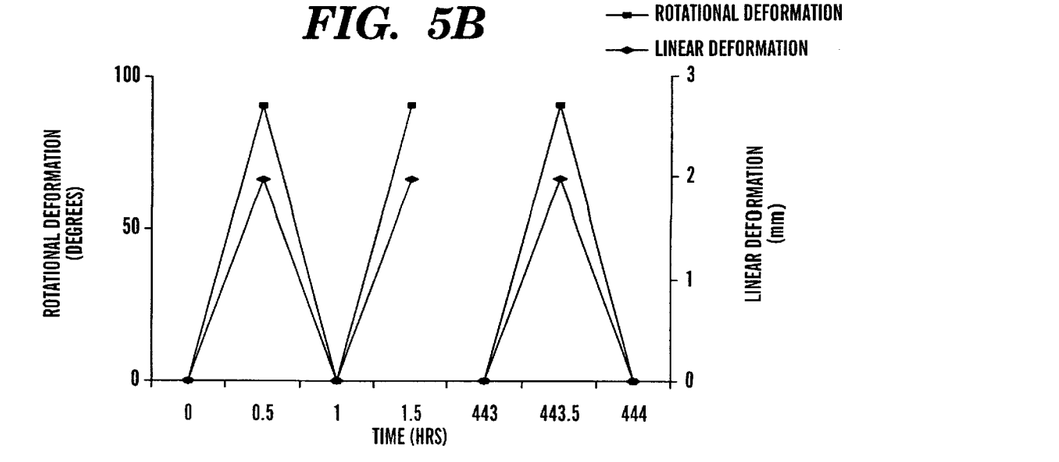

This set of studies was conducted to provide insight into the influence of frequency and cycling on ligament formation in the bioreactors (FIGS. 5a&b). After a 48 hr rest period (represented as cycle 1), the rotational and translation strain rates and linear and rotational deformation were kept constant for 18.5 days. As illustrated in FIG. 5a, the ligaments were exposed to a constant rotational and translational strain rate of 0.83% min−1 and 0.33% min−1, respectively, for 18.5 days. Rotational deformation (Δ degrees) and linear deformation (Δmm) were kept constant at 90° and 2 mm respectively. FIG. 5b shows the deformation pattern. Slopes of the plotted lines indicate strain rate.

Following the culture period, ligament samples, both the mechanically challenged as well as the controls (static) were characterized for: (1) general morphological appearance (by visual inspection); (2) cell distribution (image processing of histological sections); (3) cell orientation (histological analysis); and (4) tissue specific markers (immunostaining).

Mechanical stimulation markedly affected the morphology of the engineered ACL, the distribution of cells along the matrix, and the extracellular matrix which was generated by the cells.

The mechanical stimulation markedly affected the dimensions and overall appearance of the engineered ligaments. As compared to static controls, mechanically stimulated ligaments contracted laterally to a diameter of 5.1 mm after 21 days in culture, as compared to 6.4 mm diameter for static controls (n=3 for each group) in Experiment 3.

Figure 6A:
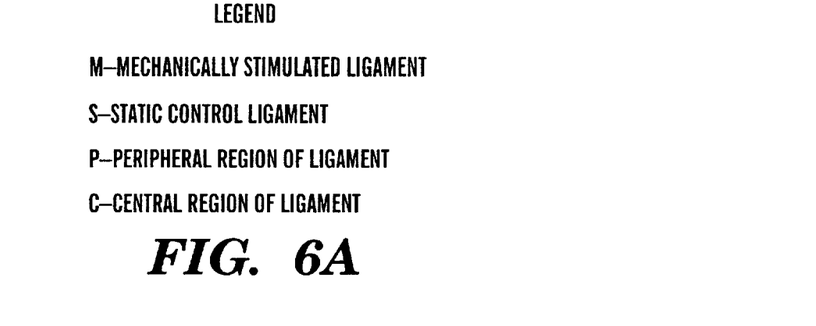
FIGS. 6 graphically illustrates the cell density data obtained from Experiment 3. *a*) Legend; *b*) Schematic diagram representing the cross sectional areas from which cell density measurements were taken; *c*) Data graphically representing the average of 8 individual cell density measurements taken from peripheral and central regions of a cross sectional area of a mechanically stimulated and a statically grown ligament.
Figure 6B:
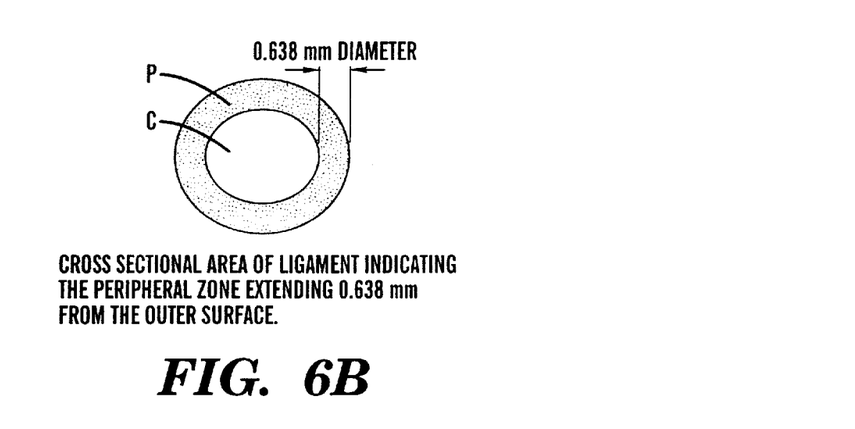
Figure 6C:
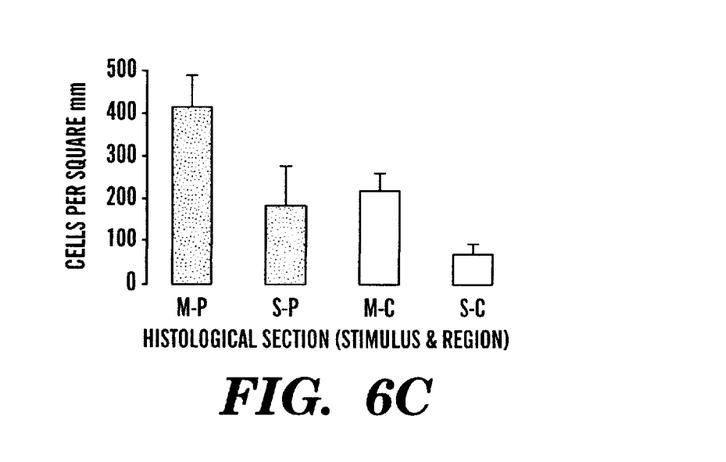

The mechanical stimulation also had a dramatic effect on cell density in the engineered ACL. Cells counts (N=8 fields, one ligament from each group,) were taken from cross sections of the control and mechanically challenged ligaments from Preliminary Experiment 3 (FIG. 6). Cell density of the ligament was approximately 3-fold higher in the center and ~2-fold higher in the periphery in the mechanically deformed ligaments in comparison to the static controls. These data indicate that mechanical stimulation provides suitable signals to the BMSCs to promote proliferation in the bioreactor environment.

The mechanical stimulation also had a dramatic effect on cell orientation. Ligament tissue samples from Experiment 3 were stained with hemotoxylin and eosin and visualized by light microscopy at 400×. Significant alignment in the BMSCs from the mechanically stimulated ligament was clearly seen, in comparison to the control (static) sample. Furthermore, this alignment had a lengthwise orientation along the longitudinal axis of the bioreactor tube, thus in the direction of the applied tension. The longitudinal orientation was similar to ligament fibroblasts found within an ACL in vivo (Woods et al. *Amer. J. Sports Med.* 19: 48–55 (1991)).

The mechanical stimulation also had a dramatic effect on the development of tissue specific markers. Collagen I accounts for ~88% of total collagen in the ACL. Collagen III accounts for ~12% of total collagen and fibronectin accounts for 2 µg/mg dry tissue weight of an ACL (Amiel et al., Ligament structure, chemistry, and physiology. In *Knee Ligaments: Structure, Function, Injury, and Repair*. Eds. Daniel, D.; Akeson, W.; O'Connor. J. Raven Press (1990)). Collagen I, collagen III and fibronectin (as indicators of new ligament tissue formation and organization) were identified by immunostaining mechanically stimulated and control (static) ligament tissue samples from Experiment 3. Mechanically stimulated ligaments expressed ligament-specific molecular markers (collagen III and fibronectin), in contrast to static controls in which the expression was either low or not detectable. The diameter of the collagen I structures observed in the mechanically challenged ligaments approached that of similar structures seen in naturally formed ACL collagen bundles, ~20 µm. The morphology of these markers suggested the beginning of differentiation of BMSCs into ligament cells and similar structural features to an ACL in terms of fiber bundle orientation and diameter.

The above results indicate that the mechanical apparatus and bioreactor system can provide a suitable environment for in vitro formation of tissue engineered ligaments starting from bone marrow stromal cells immobilized in a collagen gel matrix.

The culture conditions used in these preliminary experiments can be further expanded to more accurately reflect the physiological environment of a ligament (e.g. increasing the different types of mechanical forces) for the in vitro creation of functional equivalents of native ACL for potential clinical use. These methods are not limited to the generation of a bioengineered ACL. Indeed, by applying the appropriate magnitude and variety of forces experienced in vivo, any type of ligament in the body can be produced ex vivo by the methods of the present invention.

The above results gathered from these controlled in vitro studies of the roles of mechanical regulatory signals on precursor cell differentiation into ligament cells and in vitro development of an engineered ACL, further the understanding of the roles of mechanical regulatory signals in cell differentiation and tissue development.

METHODS OF THE INVENTION

Cell Isolation and Culture

Bone Marrow Stromal Cells (BMSC), pluripotent cells capable of differentiating into osteogenic, chondrogenic, tendonogenic, adipogenic and myogenic lineages, were chosen since the formation of the appropriate conditions can direct their differentiation into the desired ligament fibroblast cell line (Markolf et al., *J. Bone Joint Surg.* 71A: 887–893 (1989); Caplan et al., Mesenchymal stem cells and tissue repair. In *The Anterior Cruciate Ligament: Current and Future Concepts*, Ed. D. W. Jackson et al., Raven Press, Ltd, New York (1993); Young et al., *J. Orthopaedic Res.* 16: 406–413 (1998)). Bone marrow cultures were established from the tibias and femurs of 2–3 week old bovine calves. The contents of the bone marrow cavity were aseptically harvested in a 50 ml centrifuge tube containing 15 ml phosphate buffered solution (PBS) with 0.05 mM ethylene diamine tetraacetic acid (EDTA). Single cell suspensions were made by repeatedly passing the marrow through needles of different gauges (16 to 20), and resuspended in Dulbecco's Modified Eagle Medium (DMEM) supplemented with 10% fetal bovine serum (FBS), 0.1 mM non-essential amino acids (NEAA), 100 U/ml penicillin and 100 mg/L streptomycin (P/S). White blood cells were counted using a hemocytometer, plated in 100 mm Petri dishes at $2 \times 10^6$ cells per dish (approximately $25 \times 10^3$ cells/$cm^2$) in 10 ml of medium supplemented with 1 ng/ml fibroblast growth factor-2 (FGF-2) and cultured in a humidified 37° C./5% $CO_2$ incubator.

BMSCs were selected pre-plating, based on their ability to adhere to the Petri dish; non-adherent hematopoietic cells were removed with the culture medium during medium replacement. The medium was changed twice per week. When BMSC became near confluent, after approximately 2–3 weeks, upon which they were detached using 0.25% trypsin/1 mM EDTA and replated in 100 mm dishes at $3 \times 10^5$ cells per dish. After 1 more week, when dishes again became confluent, $1^{st}$ passage (P1) cells were trypsinized and 1 ml aliquots containing $20 \times 10^6$ cells (based on Goulet et al., 1997) in 1×DMEM were either seeded directly into the collagen gels or spun down and frozen in 8% DMSO 10% FBS 1×DMEM solution for future use.

The final medium in the 20 ml total volume of the reactor vessel consisted of: 5.6 ml of 3.6×DMEM at pH 8.0, 3.7 ml heat inactivated FBS (30 min at 56° C.), 9.5 ml of 4.22 mg/ml collagen [acid soluble collagen type I (Sigma type III)], 0.2 ml of 0.7 N NaOH and 1.0 ml of the cell preparation containing the $20 \times 10^6$ cells. The 3.6×DMEM consisted of 36 ml 10×DMEM containing 4500 mg glucose/L, 0.4 mg powered folic acid, 2 ml of 200 mM L-glutamine, 0.37 g sodium bicarbonate ($NaHCO_3$), 200 U/ml penicillin, 200 mg/L streptomycin, 0.5 µg/ml Fungizone (P/S and Fungizone were purchased from Life Technologies) and dd$H_2O$ to bring the volume to 90 ml; the pH was adjusted to 8.0 with 2N NaOH, and enough dd$H_2O$ to bring the final volume to 100 ml. The 3.6×DMEM solution was well mixed and filtered through a 0.2 µm filter unit and stored at 4° C.

Cell Immobilization in Collagen Matrix

To prepare an individual bioreactor tube for a ligament growth experiment $20 \times 10^6$ P1 BMSCs were resuspended in 1 ml 1×DMEM, 9.5 ml of 4.22 mg/ml bovine collagen type I, 5.6 ml 3.6×DMEM, 3.7 ml heat inactivated FBS, and 0.2 ml 0.7 N NaOH. The final concentration of collagen type I in solution was 2 mg/ml. These reagents were first added to a 50 ml centrifuge tube on ice, then quickly transferred to the bioreactor tube. The bioreactor tube was fitted with a PTFE gas filter, loaded into the mechanical device, and placed in a humidified 37° C./5% $CO_2$ incubator. The collagen was allowed to gel for 24 hours. During a 24 or 48 hr initial growth period, the ligaments were not exposed to any mechanical stimulation except for gravity to allow for sufficient adhesion to develop between the collagen matrix and the coral anchors. Fifty percent of the medium was exchanged with 10% FBS in 1×DMEM containing 200 U/ml penicillin, 200 mg/L streptomycin, 0.5 μg/ml Fungizone, after 24 hrs and two times a week thereafter.

Anchors for Ligament Matrix

Cylindrical pieces of Goinopra coral, 12 mm in diameter and 20 mm in length with a pore size of 500 μm (supplied by Interpore-Cross International) were used as the anchors. The coral was treated by a hydrothermal process to convert the calcium carbonate to calcium phosphate (hydroxyapatite). This mineral content and pore size is similar to some types of human cancellous bone and this material has been approved by the FDA for bone grafts.

Bioreactor Design

The bioreactor tube design provided an environment for the growth of a 4 cm long ligament when considering the anchors, and approximately 2 cm long extending between the anchors. The terminology used in this document will be defined as follows: (a) translation load along the longitudinal axis of the ligament—tension; (b) rotational load about the longitudinal axis of the ligament—torsion; (c) change in length ($\Delta L_t$) along the longitudinal axis of the ligament—linear deformation; (d) change in rotational degree ($\Delta L_r$) about the longitudinal axis of the ligament—rotational deformation; (e) strain ($\Delta L_t/L_{ot}$, where $L_{ot}=20$ mm initial length of ligament) along the longitudinal axis of the ligament—translational strain; (f) strain ($\Delta L_r/L_{or}$, where $L_{0r}=3\ 60°$ initial non-strained position of ligament) about the longitudinal axis of the ligament—rotational strain; (g) strain rate ($\Delta L_t/L_{ot}$/time) along the longitudinal axis of the ligament—translational strain rate; (h) strain rate ($\Delta L_r/L_{or}$/time) about the longitudinal axis of the ligament—rotational strain rate; Note: strain is reported as a percentage of $\Delta L/L_o$.

The reactor tubes and the apparatus were placed in an incubator at 37° C. with 5% $CO_2$. The reactor tubes are 2.54 cm in diameter and 10 cm long. The tubes were cut from Teflon stock tubing (McMaster-Carr Supply Co.). Each reactor tube was fitted with two nylon bulkhead-mounted luers which serve as ports for medium and gas exchange. The luers were fit within tapped holes to avoid protrusion into the inner area of the tube. The anchor mounts were machined from Teflon rod stock and a 12 mm diameter by 10 mm length hole was machined in the center of each anchor mount to allow for co-axial alignment of the coral anchors. The coral anchors were held in place with set-screws spaced 90° apart. The bottom section of the lower anchor mount and the lower translational plate, respectively, were machined with a square shape to prevent rotation of the reactor tube with respect to the translational plate. The cylindrical section of the lower anchor mount is inserted into the bottom of the teflon reactor tube and attached with a hose clamp. A stepper motor (Servo Systems, 400 steps/360°) coupled to a high precision lead screw (lead=0.635 mm/360°) and low drag torque anti-backlash nut mounted into the translational plate provide translational tolerances precise to 1.6 μm.

The upper anchor mount was attached to a rotational shaft with set screws. The shaft extended into the reactor tube through two teflon bearings. The lower of the two bearing was inserted into the top of the Teflon reactor tube and attached via a worm-drive clamp. The lower bearing did not move while allowing for the free rotation of the shaft. Super stretch silicone rubber thick was used to extend between the upper and lower teflon bearings in order to enclose the top of the reactor tube and provide a barrier against contamination.

The system used allowed for the application of a variety of loading regimes based on a combination of linear deformation (up to 2 mm and a 10% translational strain) and rotational strain (up to 25% and 90 degrees), with a collagen matrix which remained adherent to the coral anchors.

Bioreactor Operating Conditions

The coral anchors were fastened into the anchor mounts using the set screws. The upper and lower mounts, linear bearings, rotational shaft, and silicone membrane are assembled with the teflon tube. Two caps were placed on the luer ports and the reactor tube is autoclaved for 20 minutes. All materials were selected to be stable in the autoclave. After autoclaving, the upper luer cap is replaced with a Gelman Acrodisc CR PTFE 1.0 μm filter for gas exchange. The matrix and tissue culture medium containing the cells were injected through the lower port of the reactor tube using a 20 ml syringe. Following injection, the lower cap was replaced and the reactor tube inserted into the translational plate at a lowered position in the mechanical device. The translational plate was then raised so that the end of the rotational shaft extending from the reactor tube inserted into a linear bearing press fit into the rotational plate and a pin hub spur gear (120 teeth, 1.666 inch pitch diameter, Nordex) sitting above the plate. Once inserted into the gear, the rotational shaft was fastened with a set-screw. A second stepper motor (400 steps/360°) coupled to a smaller pin hub spur gear (30 teeth, 0.4166 inch pitch diameter) was used to rotate the rotational shaft and hence the top coral anchor. Since the two gears (motor gear/rotation gear) are in a 4:1 ratio, tolerances precise to 0.225 degrees can be achieved with this device.

Controls

In all experiments, control tubes consisted of identical components and conditions (cells, media, matrix, anchors) to those described for the bioreactor tube experimental set up with the exception that these tubes were not mechanically deformed (static) in the apparatus.

Software

Software used to control the mechanical device was written using C programming language and Borland C++ Compiler Version 5.0. The mechanical device was designed specifically for periodic torsional and tensile loads along the longitudinal axis of the growing ligament. The software provided precise independent control over the rotational and linear movement and the rates of these movements. Rates for linear and rotational movement range from 1 mm/day and 1°/day, respectively, to a maximum of 0.32 mm/sec and 45°/sec. The software allowed the user to input the forward and return rotational and linear rates, the duration to reach and return from the extreme points (e.g., maximum angle and distance), an intermediate period of rest or static mode at the extreme point, a rest or static mode at the home point, and the number of repetitions for the cycle. Several different cycles with varying loading regimes can be programmed and run for the duration of the experiment.

Initial Experimental Runs

In preliminary studies, up to six reactor tubes have been run concurrently for up to 21 days. A variety of loading regimes were studied to evaluate device performance, to determine ranges of conditions suitable for ligament formation, and to define limits of mechanical stress which can be applied while maintaining sufficient adhesion of the matrix to the anchors during ligament growth.

Histology and Immunohistochemistry

Samples for histological analysis were fixed in neutral buffered formalin (4%) for 24 h at 4–8° C., embedded in paraffin, and sectioned (5 μm thick) both along the longitudinal axis and in cross section through the center of the ligament. Sections were stained with hematoxylin and eosin (for cells) and trichrome (for cross-linked collagen). Polyclonal antibodies (for type I and III collagen) and monoclonal antibodies (for elastin and fibronectin) were used to determine the presence and distribution of secreted matrix components by immunofluorescence.

Cell Density, Distribution and Morphology

Spatial distributions of cells within constructs were assessed by image analysis of the hematoxylin and eosin stained cross-sections. Black and white images were acquired using an inverted microscope (Nikon Diaphot), a video camera (Hitachi HV-C20), a frame grabber card (LG-3, Scion, Frederick, Md.), and NIH-Image version 1.61 software. Fields measuring 0.30 mm$^2$ were randomly chosen and classified as either central (C) or peripheral (P), depending if the region was more or less than 0.63 mm from the outer surface of the ligament, respectively. In each field, the number of cells was determined by automated counting. For each tissue sample and time point, the average cell density was calculated from at least eight central or peripheral fields.

Cell Specific Markers

Immunofluorescence was used to determine BMSC differentiation into ligament cells, by assessing the production of specific proteins known to be necessary to maintain the overall integrity of an ACL: fibronectin, collagens I & III. Monoclonal mouse anti-bovine elastin, goat serum, and anti-mouse IgG FITC conjugate developed in goat was obtained from Sigma. Polyclonal rabbit anti-bovine type I collagen and anti-bovine collagen type III, and anti-rabbit IgG FITC developed in goat was obtained from Chemicon; polyclonal rabbit anti-human fibronectin was obtained from DAKO.

What is claimed is:

1. A method for producing an anterior cruciate ligament ex vivo, comprising the steps:
   a) providing pluripotent cells, a 3-dimensional matrix of cylindrical form comprised of collagen, and two cylindrically shaped anchors suitable for attachment to the matrix;
   b) seeding the cells in the matrix, either pre- or post-matrix formation, by means to uniformly immobilize the cells within the matrix;
   c) attaching a face of each respective anchor to either end of the seeded matrix so that the entire surface of each face of the seeded matrix of step b) contacts the face of the respective anchors; and
   d) culturing the cells in the anchored matrix of step c) under conditions appropriate for cell growth and regeneration, while subjecting the matrix to intermittent application of two or more mechanical forces via movement of one or both of the attached anchors, wherein one of the mechanical forces is tension.

2. The method of claim 1 wherein the pluripotent cells are bone marrow stromal cells.

3. The method of claim 1 wherein the seeded matrix has a concentration of collagen type I ranging from 2 mg/ml to 6 mg/ml.

4. The method of claim 3 wherein the seeded matrix has a final concentration of collagen type I of 2 mg/ml.

5. The method of claim 3 wherein the collagen is not cross linked.

6. The method of claim 3 wherein the collagen is cross-linked.

7. The method of claim 1 wherein the anchors are comprised of Goinopra coral with pore size 500 µm, the coral having been treated by means to convert the calcium carbonate to calcium phosphate.

8. The method of claim 7 wherein the Goinopra coral is further infused with fibronectin.

9. The method of claim 1 wherein the anchors are comprised of demineralized bone.

10. The method of claim 9 wherein the bone is further infused with fibronectin.

11. The method of claim 1 wherein the magnitude, duration and combination of mechanical forces are changed over the period of culture to approach that which is experienced by a native ACL in vivo.

12. The method of claim 1 wherein the mechanical forces mimic mechanical stimuli experienced by an anterior cruciate ligament in vivo.

13. The method of claim 12 wherein the anchored matrix is further cultured under conditions which mimic the chemical stimuli experienced by an anterior cruciate ligament in vivo.

14. The method of claim 12 wherein the mechanical forces comprise tension and torsion.

15. The method of claim 14 wherein the mechanical forces further comprise compression.

16. The method of claim 14 wherein tension is applied at a translational strain rate of from 0.167% min$^{-1}$ to 0.33% min$^{-1}$.

17. The method of claim 16 further comprising translational strain release at a rate of from 0.167% min$^{-1}$ to 0.33% min$^{-1}$.

18. The method of claim 14 wherein torsion is applied at a rotational strain rate of from 0.27% min$^{-1}$ to 0.83% min$^{-1}$.

19. The method of claim 18 further comprising rotational strain release at a rate of from 0.27% min$^{-1}$ to 0.83% min$^{-1}$.

20. The method of claim 14 wherein tension is applied to the ligament through a progressive linear deformation from 0 to 10% of initial ligament length.

21. The method of claim 14 wherein torsion is applied to the ligament through a progressive deformation of the ligament from 0 to 25% rotation.

22. The method of claim 14 wherein the tension is applied with a cycling frequency of from 0.05 min$^{-1}$ to 0.00417 min$^{-1}$.

23. The method of claim 14 wherein the torsion is applied with a cycling frequency of from 0.05 min$^{-1}$ to 0.00417 min$^{-1}$.

24. The method of claim 14 wherein tension is applied to the ligament through a progressive linear deformation from 0 to 10% of initial ligament length, at a rate of from 0.167% min$^{-1}$ to 0.33% min$^{-1}$, followed by tension release at a rate of from 0.167% min$^{-1}$ to 0.33% min$^{-1}$, with a cycling frequency of from 0.05 min$^{-1}$ to 0.00417 min$^{-1}$.

25. The method of claim 14 wherein torsion is applied to the ligament through a progressive deformation of the ligament from 0 to 25% rotation, at a rate of from 0.27% min$^{-1}$ to 0.83% min$^{-1}$, followed by rotation release at a rate of from 0.27% min$^{-1}$ to 0.83% min$^{-1}$, with a cycling frequency of from 0.05 min$^{-1}$ to 0.00417 min$^{-1}$.

26. The method of claim 14 wherein torsion is held at extreme points of rotational deformation for 0 to 3 hours/cycle.

27. The method of claim 14 wherein torsion is held at extreme points of translational deformation for 0 to 3 hours/cycle.

28. The method of claim 12 wherein a combination of mechanical forces are applied to simulate knee joint extension.

29. The method of claim 28 wherein the motion of knee joint extension is in the coronal plane.

30. The method of claim 28 wherein the motion of knee joint extension is in the sagittal plane.

31. The method of claim 12 wherein a combination of mechanical forces are applied to simulate knee joint flexion.

32. The methods of claim 12 wherein a combination of mechanical forces are applied which simulate a combination of flexion and extension, the combination of mechanical forces being applied over time to produce an anterior cruciate ligament which has helically organized fibers.

33. A bioengineered anterior cruciate ligament produced by the method comprising the steps:
   a) providing pluripotent cells, a 3-dimensional matrix of cylindrical form comprised of collagen, and two cylindrically shaped anchors suitable for attachment to the matrix;
   b) seeding the cells in the matrix, either pre- or post-matrix formation, by means to uniformly immobilize the cells within the matrix;
   c) attaching a face of each respective anchor to either end of the seeded matrix so that the entire surface of each face of the seeded matrix of step b) contacts the face of the respective anchors; and
   d) culturing the cells in the anchored matrix of step c) under conditions appropriate for cell growth and regeneration, while subjecting the matrix to intermittent application of two or more mechanical forces via movement of one or both of the attached anchors, wherein one of the mechanical forces is tension.

34. The bioengineered ligament of claim 33 wherein the pluripotent cells are bone marrow stromal cells.

35. The bioengineered ligament of claim 34 which is characterized by cellular orientation and/or matrix crimp pattern in the direction of the applied mechanical forces of step d).

36. The bioengineered ligament of claim 35 which is further characterized by the production of collagen type I, collagen type III, and fibronectin proteins along the axis of mechanical load produced by the mechanical forces of step d).

37. The bioengineered ligament of claim 34 wherein the mechanical forces of step d) mimic mechanical stimuli experienced by an anterior cruciate ligament in vivo.

38. The bioengineered ligament of claim 37 wherein the ligament fiber bundles are arranged into a helical organization.

39. The bioengineered ligament of claim 37 wherein the mechanical forces comprise tension and torsion.

40. The bioengineered ligament of claim 39 wherein the mechanical forces comprise tension and torsion.

41. The bioengineered ligament of claim 40 wherein the mechanical forces further comprise compression.

42. A method for producing a predetermined type of ligament or tendon ex vivo, comprising the steps:
   a) providing pluripotent cells, a 3-dimensional matrix to which cells are able to adhere, and two anchors each having a face which is suitable for attachment to the matrix;
   b) seeding the cells in the matrix, either pre- or post-matrix formation, by means to uniformly immobilize the cells within the matrix;
   c) attaching the face of each respective anchor to opposite ends of the seeded matrix; and
   d) culturing the cells in the anchored matrix of step c) under conditions appropriate for cell growth and regeneration, while subjecting the matrix to intermittent application of two or more mechanical forces via movement of one or both of the attached anchors, wherein one of the mechanical forces is tension, and the mechanical forces mimic mechanical forces experienced by the ligament in vivo.

43. The method of claim 42 wherein the pluripotent cells are bone marrow stromal cells.

44. The method of claim 42 wherein the matrix has a cylindrical form and is attached to the respective anchor faces at each face of the cylinder.

45. The method of claim 42 wherein the matrix is comprised of collagen.

46. The method of claim 45 wherein the matrix has a concentration of collagen type I ranging from 2 mg/ml to 6 mg/ml.

47. The method of claim 46 wherein the collagen is not cross-linked.

48. The method of claim 46 wherein the collagen is cross-linked.

49. The method of claim 42 wherein the anchors are further infused with a factor which promotes matrix adhesion to the anchor.

50. The method of claim 42 wherein the anchors are comprised of Goinopra coral with pore size 500 µm, wherein the coral has been treated by means to convert the calcium carbonate to calcium phosphate.

51. The method of claim 42 wherein the anchors are comprised of demineralized bone.

52. The method of claim 42 wherein the ligament produced is an anterior cruciate ligament.

53. The method of claim 42 wherein the magnitude, duration and combination of mechanical forces are changed over the period of culture to approach that which is experienced by a native ligament in vivo.

54. The method of claim 42 wherein the anchored matrix is further cultured under conditions which mimic the chemical stimuli experienced by a native ligament in vivo.

55. The method of claim 42 wherein the mechanical forces comprise torsion and tension.

56. The method of claim 55 wherein the mechanical forces further comprise compression.

57. The method of claim 42 wherein a combination of mechanical forces are applied to simulate extension of the joint in which the ligament is located in vivo.

58. The method of claim 42 wherein a combination of mechanical forces are applied to simulate flexion of the joint in which the ligament is located in vivo.

59. The methods of claim 42 wherein a combination of mechanical forces are applied which simulate a combination of flexion and extension, the combination of forces being applied over time to produce a ligament which has helically organized fibers.

60. A bioengineered ligament or tendon produced by the method comprising the steps:
   a) providing pluripotent cells, a 3-dimensional matrix to which cells are able to adhere, and two anchors each having a face which is suitable for attachment to the matrix;
   b) seeding the cells in the matrix, either pre- or post-matrix formation, by means to uniformly immobilize the cells within the matrix;
   c) attaching the face of the respective anchors to opposite ends of the seeded matrix; and
   d) culturing the cells in the anchored matrix of step c) under conditions appropriate for cell growth and regeneration, while subjecting the matrix to intermittent application of two or more mechanical forces via movement of one or both of the attached anchors, wherein one of the mechanical forces is tension and the mechanical forces mimic forces experienced by the ligament in vivo.

61. The bioengineered ligament or tendon of claim 60 wherein the pluripotent cells are bone marrow stromal cells.

62. The bioengineered ligament or tendon of claim 61 which is characterized by cellular orientation in the direction of the applied mechanical forces of step d).

63. The bioengineered ligament or tendon of claim 62 which is further characterized by collagen III fiber production and fibronectin fiber production along the axis of mechanical load produced by the mechanical forces of step d).

64. The bioengineered ligament or tendon of claim 60 wherein the mechanical forces of step d) mimic mechanical stimuli experienced by the ligament or tendon in vivo.

65. The bioengineered ligament or tendon of claim 64 wherein the ligament fiber bundles are arranged into an helical organization.

66. The bioengineered ligament of claim 64 wherein the mechanical forces comprise tension and torsion.

67. The bioengineered ligament of claim 66 wherein the mechanical forces comprise tension and torsion.

68. The bioengineered ligament of claim 66 wherein the mechanical forces further comprise compression.

69. A method for producing an anterior cruciate ligament ex vivo, comprising the steps:
 a) providing pluripotent cells, a 3-dimensional matrix of cylindrical form comprised of collagen, and two cylindrically shaped anchors suitable for attachment to the matrix;
 b) seeding the cells in the matrix, either pre- or post-matrix formation, by means to uniformly immobilize the cells within the matrix;
 c) attaching a face of each respective anchor to either end of the seeded matrix so that the entire surface of each face of the seeded matrix of step b) contacts the face of the respective anchors; and
 d) culturing the cells in the anchored matrix of step c) under conditions appropriate for cell growth and regeneration, while subjecting the matrix to intermittent application of one or more mechanical forces via movement of one or both of the attached anchors, wherein one of the mechanical forces is torsion.

70. A bioengineered anterior cruciate ligament produced by the method comprising the steps:
 a) providing pluripotent cells, a 3-dimensional matrix of cylindrical form comprised of collagen, and two cylindrically shaped anchors suitable for attachment to the matrix;
 b) seeding the cells in the matrix, either pre- or post-matrix formation, by means to uniformly immobilize the cells within the matrix;
 c) attaching a face of each respective anchor to either end of the seeded matrix so that the entire surface of each face of the seeded matrix of step b) contacts the face of the respective anchors; and
 d) culturing the cells in the anchored matrix of step c) under conditions appropriate for cell growth and regeneration, while subjecting the matrix to intermittent application of one or more mechanical forces via movement of one or both of the attached anchors, wherein one of the mechanical forces is torsion.

71. A method for producing a predetermined type of ligament or tendon ex vivo, comprising the steps:
 a) providing pluripotent cells, a 3-dimensional matrix to which cells are able to adhere, and two anchors each having a face which is suitable for attachment to the matrix;
 b) seeding the cells in the matrix, either pre- or post-matrix formation, by means to uniformly immobilize the cells within the matrix;
 c) attaching the face of each respective anchor to opposite ends of the seeded matrix; and
 d) culturing the cells in the anchored matrix of step c) under conditions appropriate for cell growth and regeneration, while subjecting the matrix to intermittent application of one or more mechanical forces via movement of one or both of the attached anchors, wherein one of the mechanical forces is torsion, and the mechanical forces mimic mechanical forces experienced by the ligament in vivo.

72. A bioengineered ligament or tendon produced by the method comprising the steps:
 a) providing pluripotent cells, a 3-dimensional matrix to which cells are able to adhere, and two anchors each having a face which is suitable for attachment to the matrix;
 b) seeding the cells in the matrix, either pre- or post-matrix formation, by means to uniformly immobilize the cells within the matrix;
 c) attaching the face of the respective anchors to opposite ends of the seeded matrix; and
 d) culturing the cells in the anchored matrix of step c) under conditions appropriate for cell growth and regeneration, while subjecting the matrix to intermittent application of one or more mechanical forces via movement of one or both of the attached anchors, wherein one of the mechanical forces is torsion and the mechanical forces mimic forces experienced by the ligament in vivo.

* * * * *